Figure 1:
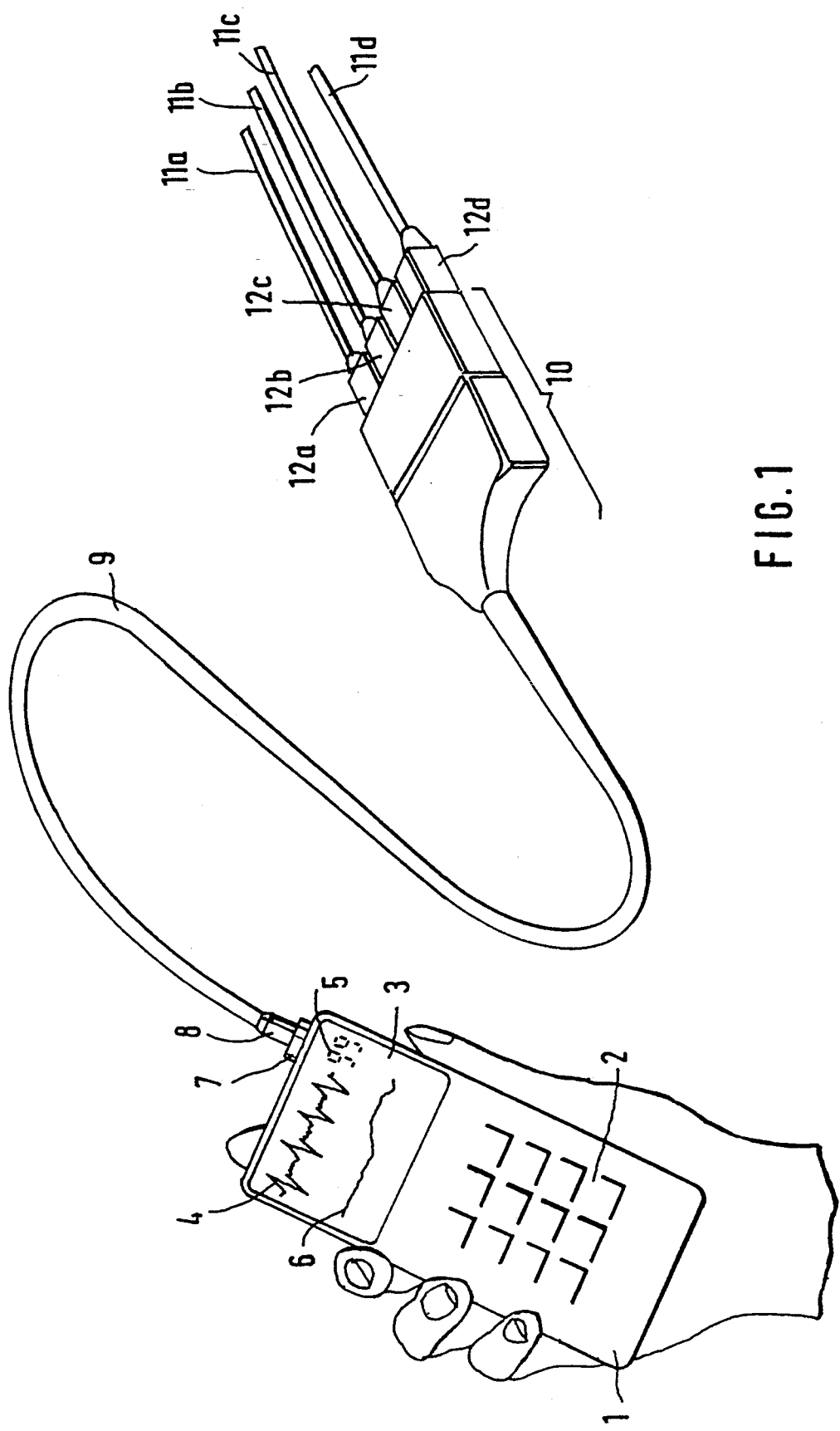

United States Patent [19]
Pross et al.

[11] Patent Number: 5,343,869
[45] Date of Patent: Sep. 6, 1994

[54] METHOD AND SYSTEM FOR MONITORING VITAL SIGNS

[75] Inventors: Gerhard Pross, Weil im Schoenbuch; Malte Schlueter, Boeblingen, both of Fed. Rep. of Germany

[73] Assignee: Hewlett Packard Company, Palo Alto, Calif.

[21] Appl. No.: 1,183

[22] Filed: Jan. 7, 1993

[30] Foreign Application Priority Data

Jan. 29, 1992 [EP] European Pat. Off. ........ 92101398.3

[51] Int. Cl.⁵ .......................................... A61B 5/0404
[52] U.S. Cl. .................................... 128/700; 128/710
[58] Field of Search ............... 128/670, 671, 682, 696, 128/700, 736, 903, 710

[56] References Cited

U.S. PATENT DOCUMENTS

| | | | |
|---|---|---|---|
| 4,125,111 | 11/1978 | Hudspeth et al. | 128/2.05 T |
| 4,356,486 | 10/1982 | Mount | 340/870.38 |
| 4,916,441 | 4/1990 | Gombrich | 340/712 |
| 4,982,738 | 1/1991 | Griebel | 128/670 |
| 5,002,062 | 3/1991 | Suzuki | 128/710 |
| 5,003,984 | 4/1991 | Muraki et al. | 128/903 |
| 5,238,001 | 8/1993 | Gallant et al. | 128/700 |

FOREIGN PATENT DOCUMENTS

| | | | |
|---|---|---|---|
| 0371424 | 6/1990 | European Pat. Off. | 128/670 |
| 0444934 | 9/1991 | European Pat. Off. | 128/700 |
| 0466272 | 1/1992 | European Pat. Off. | 128/700 |
| 8908398 | 9/1989 | Fed. Rep. of Germany | 128/700 |

*Primary Examiner*—George Manuel

[57] ABSTRACT

A portable hand-held monitor (1) for monitoring vital signs is connected, via a single connector (7), with a cable (9). This cable ends up in a combiner (10) which, in turn, receives plugs (12a to 12d) leading, via cables (11a to 11d), to single sensors or transducers applied to a patient. Portable hand-held monitor (1) comprises a display (3) and internal memory means, in order to store recorded vital signs and to transmit them to a remote computer later on. As only a single cable (9) is required for connection with combiner (10), patient monitoring becomes quite easy if the combiner (10), cable (9) and the associated sensors and interconnection cables are left at or near the patient. In this case, a plug (8) connected with cable (9) has simply to be inserted into connector (7), in order to start data acquisition. The same simple approach may be used to monitor the next patient, and so on.

17 Claims, 11 Drawing Sheets

METHOD AND SYSTEM FOR MONITORING VITAL SIGNS

The present invention relates to a method for retrieving and/or monitoring vital signs of a patient, wherein $n \geq 2$ sensors, such as electrocardiogram electrodes, a temperature sensor or a cuff for measuring non-invasive blood pressure, are applied to a patient, according to the preamble of claim 1. As will be discussed later, the invention also relates to a corresponding system for retrieving and/or monitoring vital signs of a patient.

In clinical practice, there are a multiplicity of applications for monitoring or recording the vital signs of a patient, such as the heart rate, temperature, respiration, blood pressure or oxygen saturation, but also other information which cannot be directly measured by an instrument such has skin color or personal well-feeling. Some of these applications require permanent monitoring of the patient, such as in the intensive care unit or in the operating room, where the immediate generation of alarms or alerts—in case a vital sign deviates significantly from what was expected—is a "must" requirement. Therefore, in such critical applications, several patient parameters need permanent monitoring by appropriate equipment.

However, there are also other applications where continuous monitoring of the patient is not required. One example of this kind is the regular (e.g. daily) routine check by a nurse in the hospital, wherein parameters such as temperature, blood pressure and pulse are measured and recorded; further, related information such as medications, clinical events and the like are retrieved. Another example is medical examination in a doctor's practice, or in a rehabilitation center. Yet another example is patient monitoring during transport.

In the past, such checks or examinations have been performed manually; e.g., the blood pressure was determined with the auscultatory technique using an inflatable cuff and a stethoscope. Likewise, the temperature or the pulse were measured manually. The results of the tests were then documented manually on a hospital form.

It will be appreciated that this is a laborious and time-consuming method. However, even if one would use automatic stationary monitors, such as an automatic non-invasive blood pressure (NIBP) monitor, this would not solve the underlying problem, as an expensive NIBP or other monitor would be required for every bed, although measurements would only be taken very rarely (e.g. once per day). Even if one would share such a monitor among multiple patients, it had to be disconnected from one patient before it could be connected to the next, thus requiring either move of the monitor or of the patient. This method would thus not relieve the nurse from complicated manual routine, and it would be expensive as well. A further disadvantage of this method is that vital signs or other related information which is not subject to automatic measurement, such as medication, can neither be monitored, nor recorded on an automatic basis. Therefore, manual documentation is still necessary. By the way, manual documentation will also be necessary for other purposes, as most common monitors, e.g. NIBP or temperature monitors, do not provide printout capability, such as a built-in recorder.

There have been attempts to solve the underlying problem by means of portable monitors (which can be carried by the nurse). For example, U.S. Pat. No. 4,916,441 describes a portable hand-held terminal of this kind. The hand-held terminal may be carried by the nurse or the physician during patient visit, and later be connected with a personal computer or a hospital information system, in order to transmit data collected during patient visit from the portable unit to the remote system.

However, the disadvantage of this kind of portable unit is that all data entry has to be made manually (via a touch screen keypad, an alphanumeric keyboard or a bar code reader). That is, even measurements which could be made on an automatic basis (like blood pressure or temperature measurement) have to be made manually, and the acquired data (e.g., the thermometer reading) have then to be entered (also manually) into the portable hand-held terminal.

The known portable unit thus does not relieve medical personnel from performing manual measurements, but rather replaces the manual documentation in writing by "quasi"-automatic data acquisition ("quasi"-automatic here means that manual operation, i.e. manual entry of all vital signs information including blood pressure and temperature values, heart rate etc. is still necessary). This does not save a considerable amount of time. Further, although pencil and paper are no longer required, other complex tasks have now to be performed instead, such as multiple user identification etc. Therefore, the portable terminal described above does not adequately solve the underlying problem.

Another hand-held physiological monitor is described in WO 89/00024. This monitor provides connections to appropriate sensors, in order to receive electrocardiogram, temperature and respiration data. A "specialist module" attachable to the main unit is used to measure other parameters, such as transcutaneous gases, pH or non-invasive blood pressure.

The latter hand-held physiological monitor is thus able to retrieve and monitor vital signs data by means of automatic data acquisition (e.g., temperature may be read in automatically, without the need to type the temperature value, or to operate a bar code reader). Thus, it reduces in fact the necessary efforts, and the time spent, by clinical personnel.

However, there are still several aspects which limit the clinical applicability, and ease of use, of the known hand-held physiological monitor. These are particularly:

In order to perform a measurement, a multiplicity of connections have to be made—the electrocardiogram electrodes have to be connected with a "patient cable input", the temperature sensor with a temperature probe input, and another sensor with the sensor connector of the "specialist module". The task of connecting and disconnecting each patient is therefore still laborious;

only one "specialist module" may be attached to the main unit—therefore, it is impossible to monitor multiple parameters not supported by the main unit (e.g., $pO_2$ and non-invasive blood pressure) simultaneously;

the known hand-held physiological monitor is not fully configurable, i.e. a parameter not required in a certain application (such as respiration) cannot be removed and replaced with another parameter of interest, such as oxygen saturation;

in case a multiplicity of patients with different demands have to be monitored by the nurse as she is making her round (as will be usually the case), she will have to carry multiple "specialist modules" with her and exchange them from patient to patient.

It is a major object of the present invention to provide a method, and a system of the kind described above which avoid most, or all of the disadvantages of the prior art devices. In particular, it is a goal of the invention to provide a method and a system for retrieving and/or monitoring of vital signs which makes handling very easy for clinical personnel. In a preferred embodiment, it is also a goal to provide a system able to store the vital signs information, as will be discussed below.

According to the present invention, this object is achieved, in a method of the kind described above, by the following steps:

connecting said n sensors to combining means,
linking the combining means to an electronic data acquisition unit, preferably a portable electronic data acquisition unit and in particular a hand-held monitor, via $m < n$ linking means,
retrieving vital signs information from at least one of said n sensors and feeding it, via said combining means, to said electronic data acquisition unit.

That is, n sensors are connected to the patient. Still there are less connections to the electronic data acquisition unit, namely m connections wherein m is smaller than n ($m < n$). This is achieved by providing combining means which effectively reduce the number of connections required. The combining means are then connected via linking means to the electronic data acquisition unit which is preferably a portable hand-held monitor.

It is a major outstanding advantage of the present invention that only few, ideally only one, connections are required between the combining means and the electronic data acquisition unit. The sensors, as well as the combining means, may be left at or near the patient. This does not cause considerable cost, as the sensors or combining means are not very expensive. On the other hand, intervallic patient monitoring becomes quite easy, as only few connections, in particular a single connection, have to be established to the monitor when the nurse goes around to gather the vital signs of a multiplicity of patients.

The invention could also be expressed as a method for retrieving and/or monitoring vital signs of a patient, wherein at least two sensors, such as electrocardiogram electrodes, a temperature sensor or a cuff for measuring non-invasive blood pressure, are applied to a patient, which is characterized by the steps of:

connecting the at least two sensors to a combiner,
connecting the combiner to an electronic data acquisition unit, preferably a portable electronic data acquisition unit and in particular a hand-held monitor, via a single connector or cable or at least a single connector or cable,
retrieving vital signs information from at least one of the at least two sensors and feeding it, via the combiner, to the electronic data acquisition unit.

In this second formulation of the present invention, it is said that the combining means is a combiner, which is a preferred embodiment of the invention. However, it will be appreciated that other solutions to provide combining means, such as feeding electrical leads to a common sheath, or providing a non-invasive blood pressure cuff which combines the leads of various electrodes, may be used as well. (The latter examples will be discussed below).

Further, the second formulation of the invention uses the term "connecting" for the interrelation of the combiner/combining means and the electronic data acquisition unit, rather than the term "linking" used in the first formulation. This difference also expresses a preferred embodiment of the present invention: Connection means, in particular electrical connection means, are the preferred means for linking the combiner/combining means and the electronic data acquisition unit. However, other solutions such as telemetric transmission (e.g., wireless transmission using electromagnetic radiation, ultrasound, infrared light etc.) are also possible and may be advantageous in certain embodiments.

The first formulation of the present invention says that a number of linking means is provided which is smaller than the number of sensors. As outlined above, already this feature implies certain serious advantages over the prior art. However, it will be appreciated that the preferred solution is to provide a single cable or connector only, in particular a single electrical cable or connector.

It will be understood that the relation $m < n$ may be read on the linking means as such, as well as only on electrical cables or connectors. In the latter case, it may occur that n sensors are connected via $m < n$ electrical cables, but also by additional linking means of another type, such as a pneumatic tube (which is required to perform non-invasive blood pressure monitoring). It is understood that such cases are covered by the present invention as well.

For easier understanding, the following explanation focuses on the second formulation of the present invention, but without limitation to this embodiment.

According to the new method, the cables of at least two different sensors are fed to a combiner (i.e. a common connector, or the like). The combiner is usually placed near the patient (e.g., fixed to its bed via a clamp) and connectable with the electronic data acquisition unit via a single cable.

Therefore, only a single connection is required between the sensors and the electronic data acquisition unit. Data acquisition thus becomes very easy: The nurse has simply to put one connector plug into the jack of the electronic data acquisition unit (or vice versa), in order to gather vital signs information of a patient.

In particular, it is possible to apply certain sensors (such as electrocardiogram electrodes, a temperature sensor, or an oximetry sensor) to a patient permanently, or at least for a longer time period. The sensors are connected with said combiner, and the combiner is left near the patient. When the nurse enters the room, she has simply to connect the electronic data acquisition unit with the combiner, and wait until the required vital signs information has been transmitted. The same may happen the next day, and so on.

Likewise, it is easy to monitor a multiplicity of patients as the nurse is making her round. She may simply walk from bed to bed, connect a patient to her electronic data acquisition unit with a single movement, disconnect the patient, and then she is ready to connect the next patient. This makes handling quick, easy and comfortable, and does not require expensive equipment. She may also type patient or vital signs information not subject to automatic data acquisition (e.g., medications) directly on a keypad or the like of the electronic data acquisition unit.

The method according to the present invention also provides full flexibility, as all sensors required for a specific patient may preferably be connected with the combiner. The set of sensors used may be different from patient to patient; however, there is no need to replace equipment as the nurse moves around. There is also no limitation in the selection of vital signs (as in the physiological monitor according to WO 89/00024, wherein only one of the "special" parameters can be monitored).

The present invention also avoids any confusion and cable mix-up encountered when a multiplicity of cables have to be operated and connected.

Typical vital signs suited for retrieving and/or monitoring according to the present invention include:
electrocardiogram
pulse
respiration
temperature
oxygen saturation
non-invasive blood pressure
invasive blood pressure
blood gases and pH
and so on.

It is understood that these vital signs need not necessarily be stored, monitored or otherwise processed as real-time waves. Instead, it is also possible to process trend values, histograms, mean values or other derived parameters which allow a greater degree of data compression. For example, instead of processing the electrocardiogram, the pulse (heart rate) could be used instead.

The single cable between the combiner and the electronic data acquisition unit is not the only solution suited for practicing the present invention. Instead, the combiner may be directly applied to a single jack or the like incorporated in the electronic data acquisition unit, such that no intermediate cable is necessary. Further, more than one cable may extend between the combiner and a single connector provided for connection with the electronic data acquisition unit. Such a design may particularly be chosen if the monitoring capability covers non-invasive blood pressure; in this case, an electrical cable, as well as a pneumatic tube or hose, will extend beyond the combiner and a connector. All of these environments are covered by the present invention.

The application of the present invention is further not limited to hospitals. It may also be useful in the doctor's practice, in obstetrical care units, rehabilitation centers, the introduction room, the neonatal ward, in an emergency vehicle or emergency case, at the patient's home, in the exercise room, industry centers, upon home visits and the like. It may also be used for quasi-"permanent" monitoring of a patient during transport (e.g., in an emergency vehicle, or during patient transport from the introduction room to the operating theatre, or from the operating room to the recovery room), in particular if it is a portable hand-held monitor. In such cases, the electronic data acquisition unit may be connected with the patient over longer time periods and accompany him, and it provides complete monitoring, e.g. from an event (like a car crash) and during the ambulatory situation and transport, until the patient arrives in the hospital. If the electronic data acquisition unit is equipped with storage capabilities, as will be discussed below, the complete patient history can be recorded.

Preferably, the electronic data acquisition unit is portable, in particular a hand-held monitor. However, the present invention is not limited to this kind of data acquisition unit. Instead, the combiner approach makes it useful for stationary monitors, and other medical devices, as well. Consider, for example, a hospital with an introduction room, an operating theatre and a recovery room. As the patient is moved from one of these rooms to the next, the applied sensors, and the combiner, may accompany him (i.e., they are not removed), whereas he will be connected with different stationary electronic data acquisition devices in every room. In this case, the single cable/connector approach makes interconnection with the various stationary monitors easy, as only a single connection has to be established.

In one preferred embodiment, the inventive method is further characterized by the step of displaying the vital signs information on a display, preferably a liquid crystal display, built in the electronic data acquisition unit. This makes immediate control of the patient's condition easy, even if the retrieved vital signs information is also used for other purposes, as will be discussed below. Alarms etc. may also be provided.

In another advantageous embodiment, the additional step of storing the vital signs information in the electronic data acquisition unit is provided. The information is stored for later processing. In particular, if vital signs information has been stored in a portable electronic data acquisition unit, the following additional steps may preferably be performed:
connecting the portable electronic data acquisition unit to a remote computer, in particular a personal computer or a remote hospital computer, and
transmitting the vital signs information stored in the portable electronic data acquisition unit at least partially to the remote computer.

The vital signs information collected from a patient, or from a multiplicity of patients, may thus be "downloaded" to a remote computer for further processing. In particular, the remote computer may be able to calculate further derived parameters, generate a printout, and the like. The data may further be used in a hospital information system which is also used to administer other data, e.g. diagnostic data and/or administrative data. In case the remote computer is a personal computer, it may be located in the nurse's office or the like. It may also be a laptop computer, etc.

According to another, most advantageous embodiment of the present invention, patient information is transmitted from the remote computer to the portable electronic data acquisition unit. That is, the patient's name, his clinical history, an administrative number assigned to the patient, his health insurance or related data may be "uploaded" from the remote system to the portable electronic data acquisition unit. The nurse may recall this information at any point in time as she is making her round. A patient identifier is particularly helpful if vital signs of a multiplicity of patients are to be collected. In this case, the nurse may recall the pre-stored patient identifier prior to data acquisition, such that the vital signs information is correctly assigned to a particular patient. This may be done by a simple keystroke. Another keystroke may cause the portable electronic data acquisition unit to store the vital signs information of the patient.

The data uploaded from a remote computer to the portable electronic data acquisition unit may also comprise patient care-related information, alarming information or scheduling information. In case of the nurse's schedule, she may always check her duties as she is making her round, and she may even be alarmed or alerted automatically (e.g., by means of an optical or acoustic alarm) of appointments and the like.

A patient care plane could also be uploaded. The portable monitor may remind the nurse of medications and other treatments due, either by displaying the care plan, or by an acoustic alarm. Further, the portable monitor may request a confirmation of effected patient treatment, and store the confirmation. If this information is later transmitted to a remote computer, a complete history, including control over performed measures, is available.

An alarm function (optical, acoustic or otherwise) may also be provided in case a parameter—e.g., heart rate—, exceeds a limit.

The invention also relates to a system for retrieving and/or monitoring a multiplicity of vital signs of a patient, comprising at least two sensors, such as electrocardiogram electrodes, a temperature sensor or a cuff for measuring non-invasive blood pressure, for appliance to the patient, and at least two connection means, in particular electrical cables or a pneumatic tube, each of the connection means being assigned to one of the sensors.

In the terms used herein, a "multiplicity" of vital signs means at least two. The above system is characterized by the following features:

a combiner provided for connection, preferably releasable connection, with at least two of the connection means, and an electronic data acquisition unit, preferably a portable electronic data acquisition unit and in particular a hand-held monitor, connectable or linkable with said combiner via (at least) a single connector or cable.

This concept may be expanded as stated in the claims, i.e., by m<n linking means between combining means and the electronic data acquisition unit, for n≧2 sensors and n≧2 connection means.

As already mentioned above, the inventive electronic data acquisition unit comprises preferably a display, e.g. a liquid crystal display, for displaying the vital signs information, and/or memory means for storing the vital signs information. In the latter case, if the electronic data acquisition unit is a portable one, it may advantageously be connectable with a base station. The base station may be a computer, or it may be connectable with a remote computer, in order to exchange data with the portable electronic data acquisition unit, e.g. for "download" of vital signs information, or for "upload" of patient data.

The portable electronic data acquisition unit may advantageously be provided with data input means, e.g. a small keyboard or a touch keypad, such that recall of patient information is easy. Further, such input means may be used to enter information which cannot be measured on an automatic basis, for example medication or clinical events, or for confirmation purposes.

In case a base station is provided, it comprises preferably supporting means for the portable electronic data acquisition unit. Electrical connection with the base station and/or a remote computer may then be established by means of an electrical cable plugged into the portable unit, or—in a preferred embodiment—in that the supporting means of the base station includes automatic electrical connection means, in particular an electrical connector at the bottom of the supporting means, which engage with corresponding electrical connection means at the bottom of the portable electronic data acquisition unit. Further, such electrical connectors may be used to recharge a battery in the portable unit.

The base station may further comprise a recorder, such that an immediate printout of the vital signs information (e.g., the electrocardiogram) is possible, and/or a housing for accessories, which may be used by the nurse such that anything required for her patient visits is at a single location.

In a preferred embodiment of the present invention, a memory is integrated into a memory module, and the memory module is insertable into a remote station which preferably contains a multiplicity of insertion slots. Each memory module may e.g. be assigned to a specific patient, or to a group of patients. It is thus possible to store and later download vital signs information, or to upload patient-care related or other information, in patient-specific manner.

The memory modules may be inserted into a remote station able to house one, or a multiplicity, of such memory modules, in order to download vital signs information, or to upload the patient care plan, the nurse's schedule and the like. For this purpose, the remote station may be equipped or in connection with a personal or host computer. In a preferred embodiment, the remote station is connected with a host computer via a wireless link, such that the remote station may be located e.g. in the nurse's office, or that the nurse may even carry it with her as she is making her round.

Advantageously, a display/memory module is used; i.e., the display and the memory are contained in a removable module. However, this is not a mandatory requirement of the present invention.

, As already mentioned, a blood pressure cuff may also be used as combining means. Such cuffs are required for non-invasive blood pressure monitoring. According to an important and most advantageous embodiment of the present invention, an electrode, or a multiplicity of electrodes, or sensors of other kind, may be integrated into such a cuff, preferably at its inner wall. Examples of suitable electrodes are an electrocardiogram electrode, a respiration electrode, or an oxygen saturation (preferably pulse oximetry) sensor. The wiring may then be performed inside the cuff, or in the walls of the cuff. A pneumatic tube and an electrical cable connect the cuff with the electronic data acquisition unit. Instead, the electrical leads may also be integrated into the walls of the pneumatic tube. It is understood that this aspect of the invention may also be used separately of, i.e., without the other features of the present invention.

The invention also relates to an electronic data acquisition unit for medical purposes, comprising a portable housing and characterized by a single connector for receiving a multiplicity (at least two) of vital signs of a patient. The housing of this electronic data acquisition unit includes preferably a display, a memory and/or a key pad. The memory may be removable, as outlined above.

Further important aspects of the present invention will be found in the claims and the detailed description.

Figure 2A:
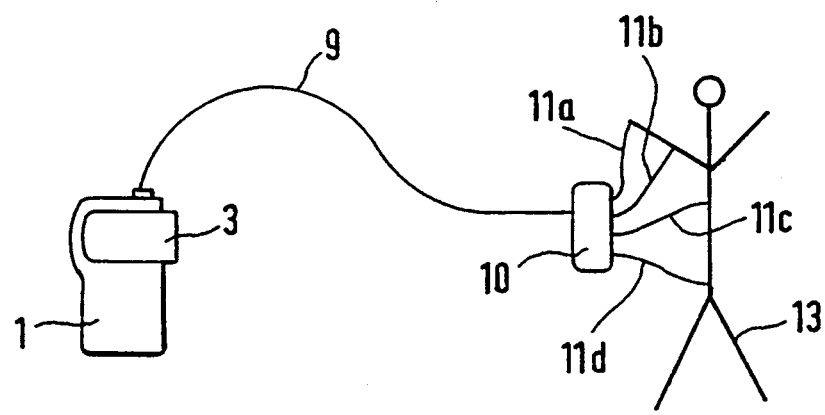
Figure 2B:
Figure 2B:
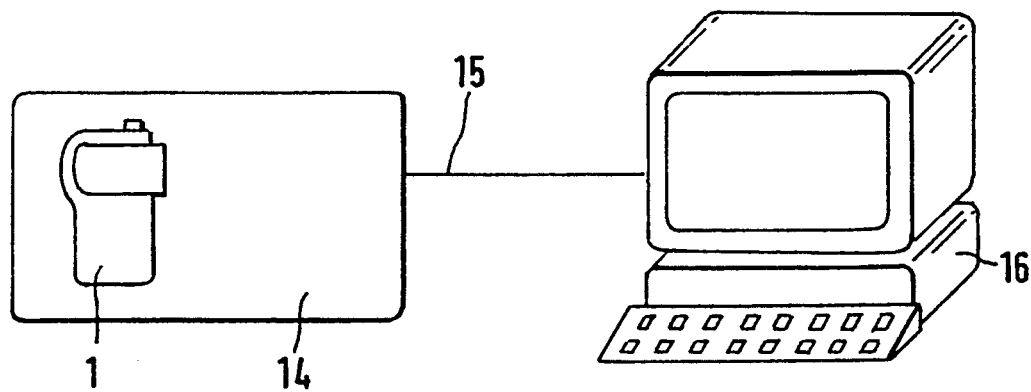
Figure 3:
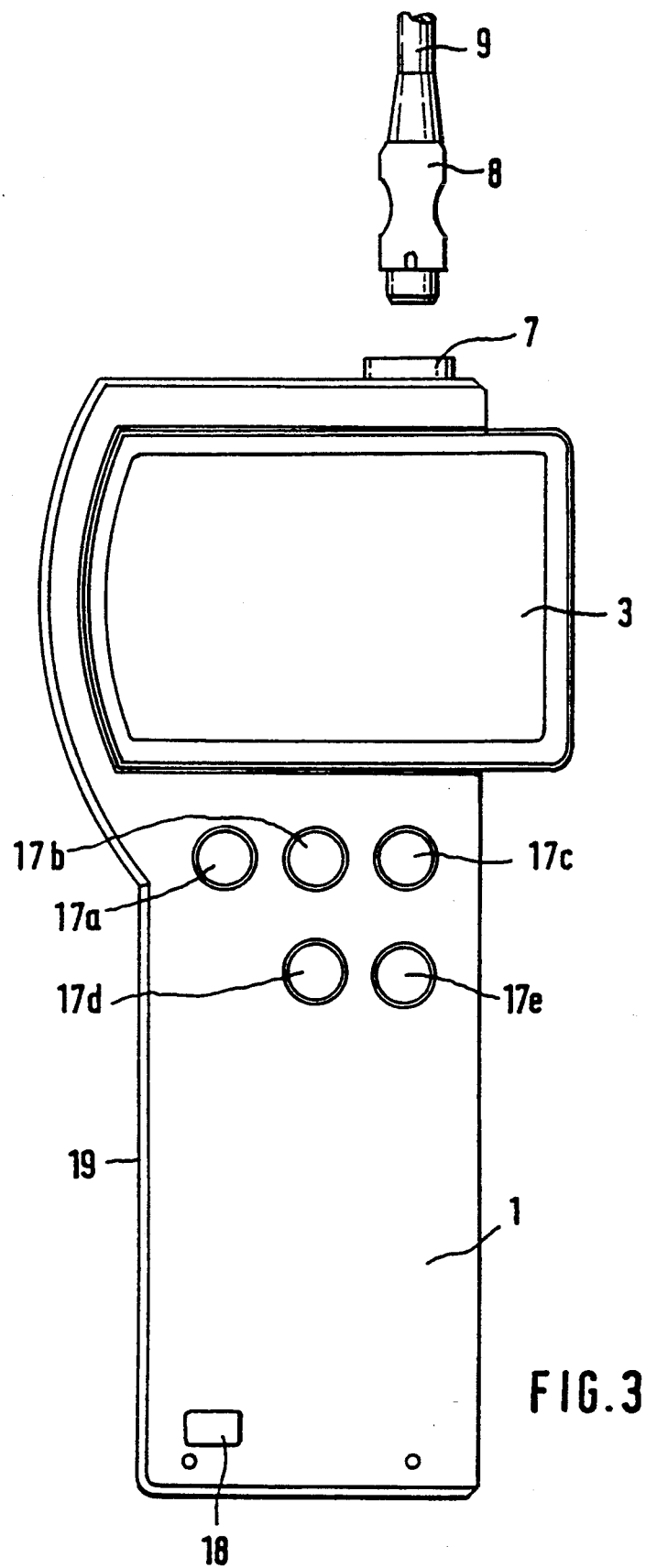
Figure 4:
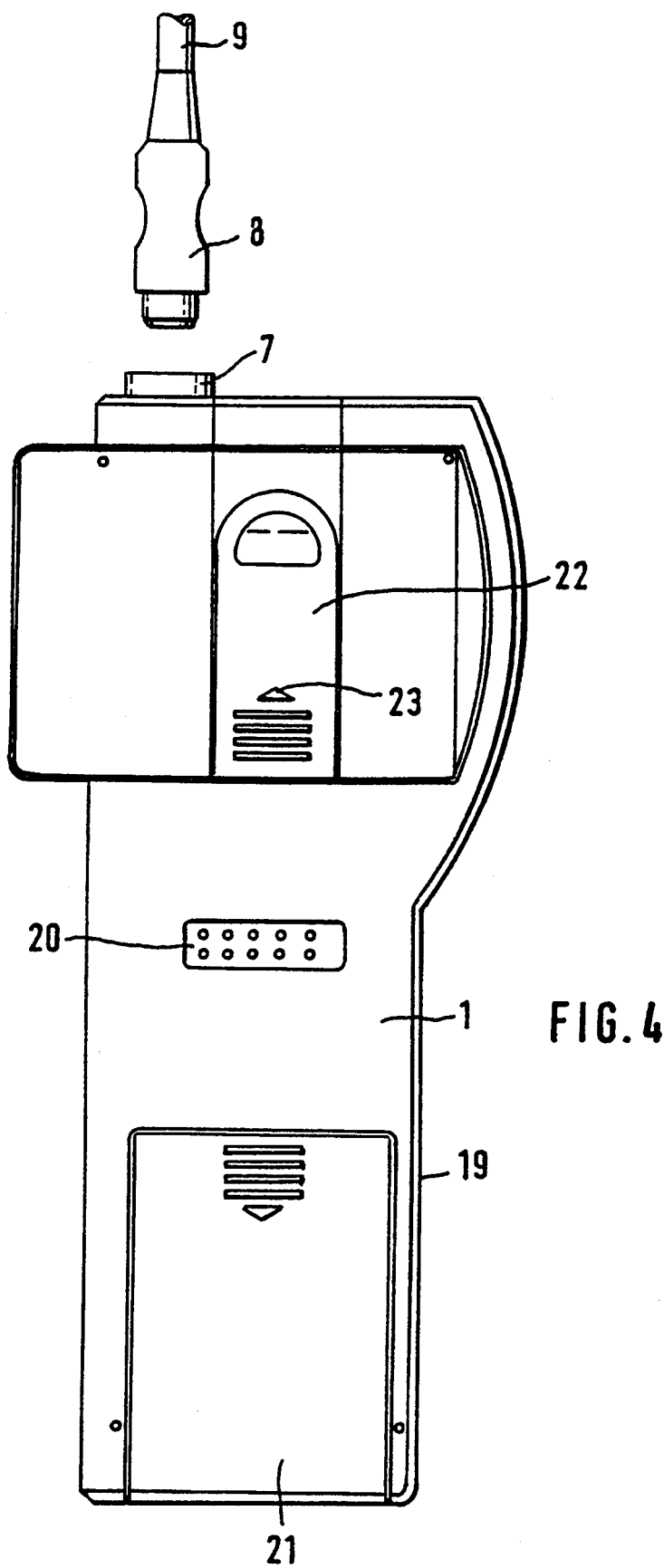
Figures 5A, 5B:
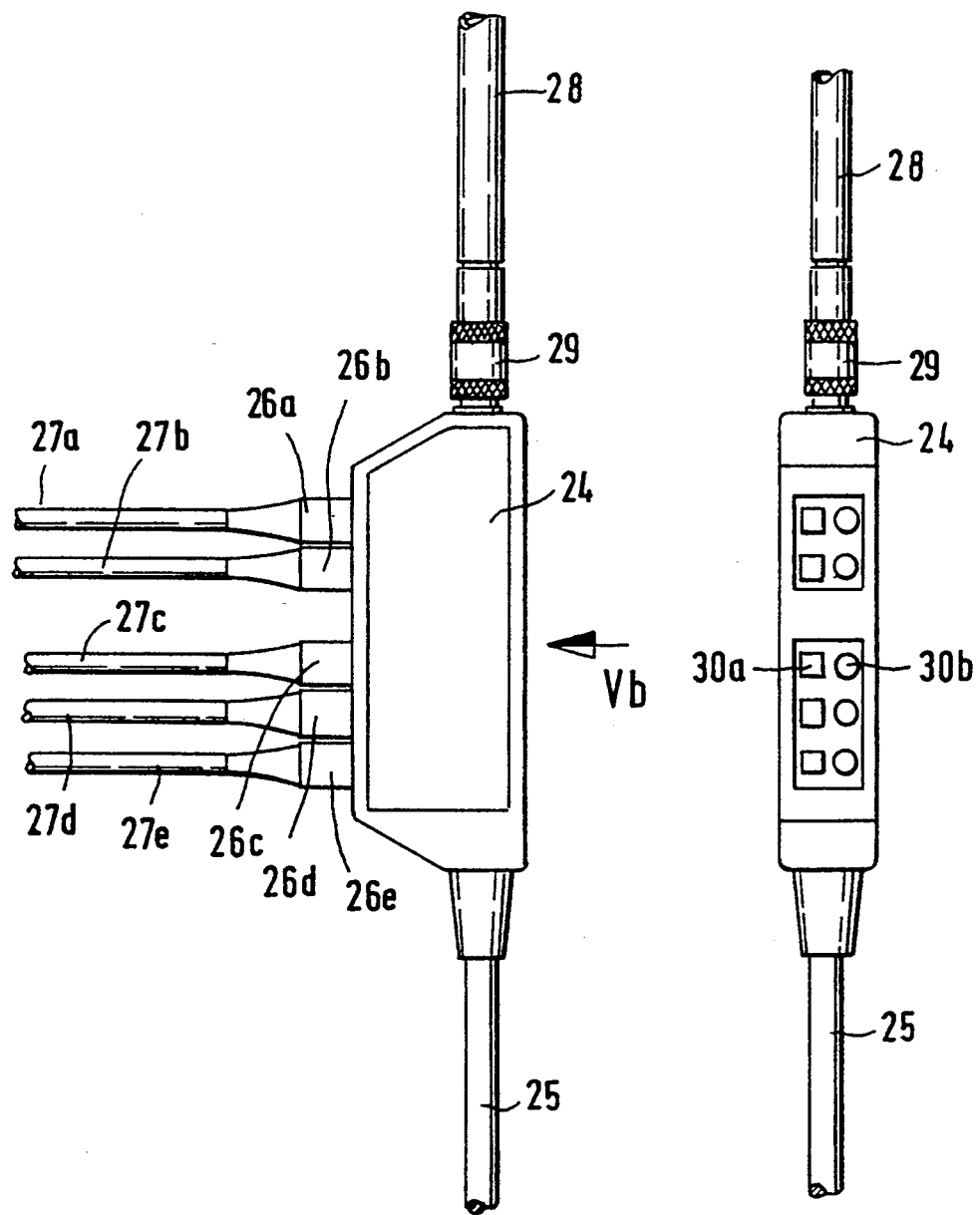
Figure 6:
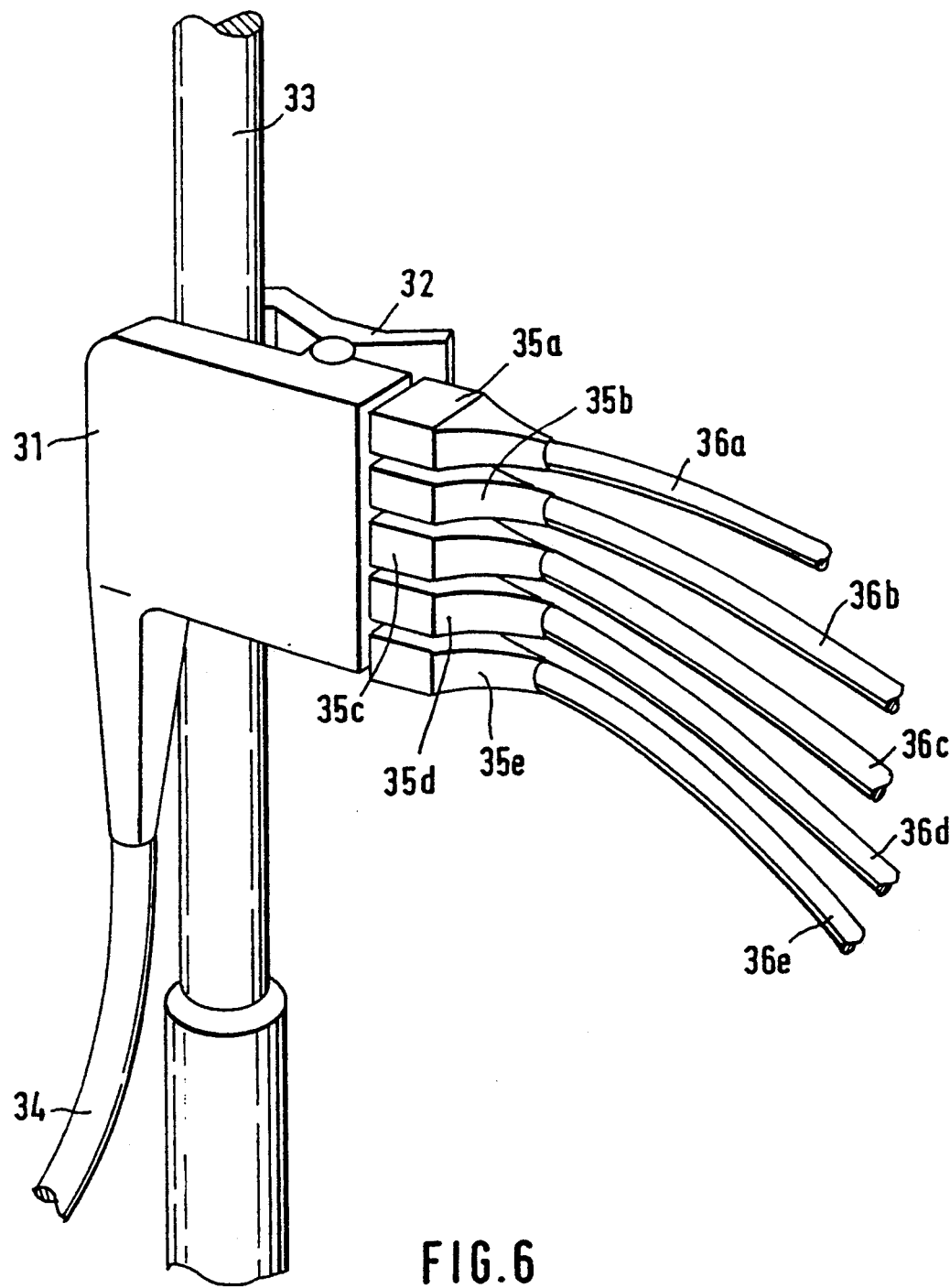
Figure 7:
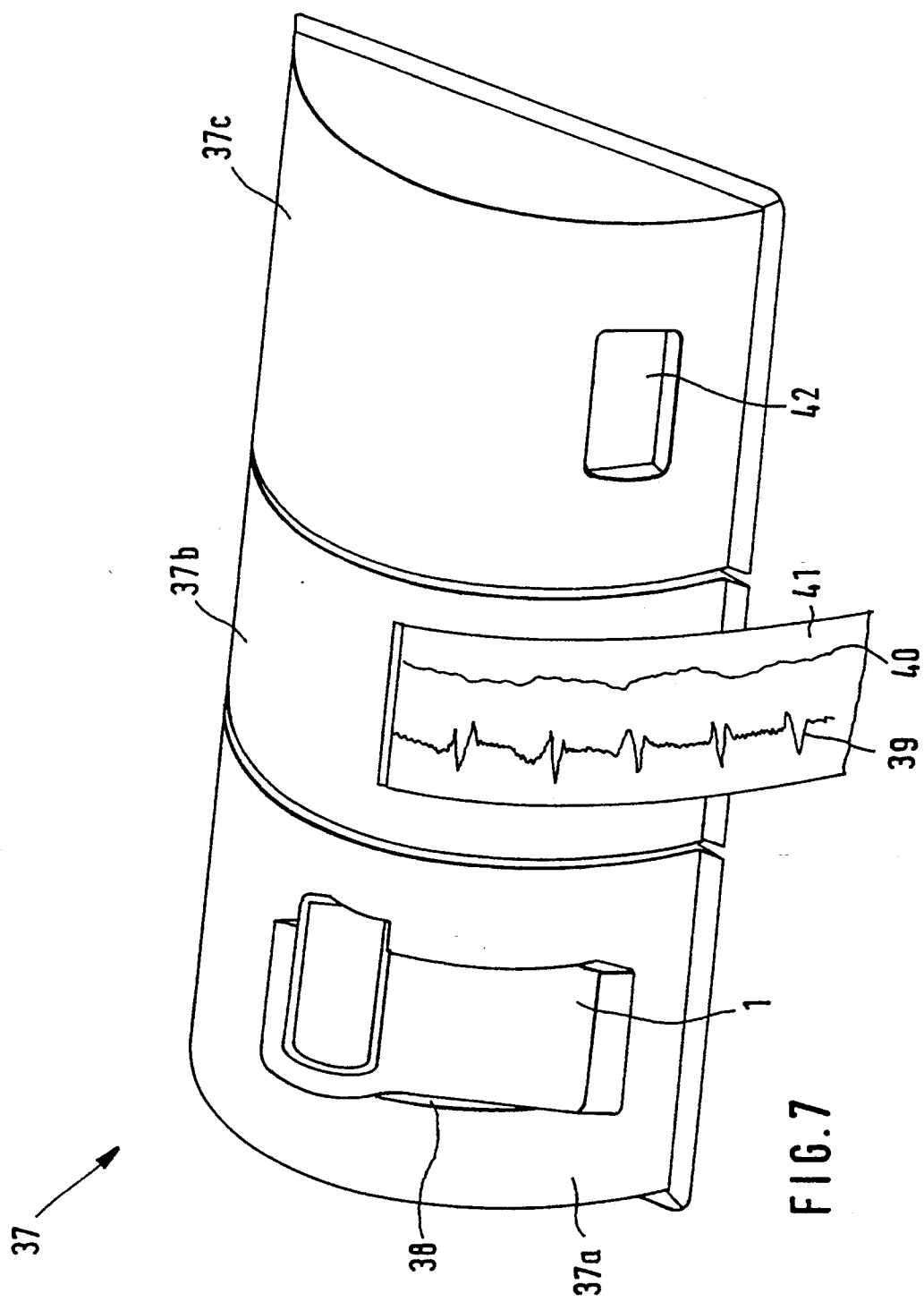
Figure 8:
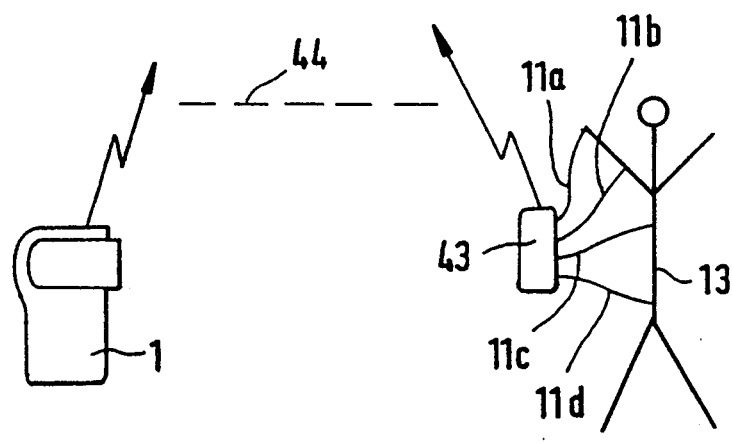
Figure 9:
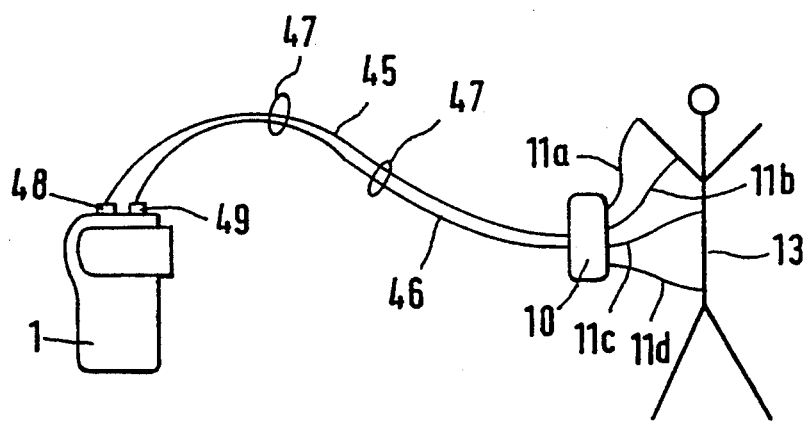
Figure 10A:
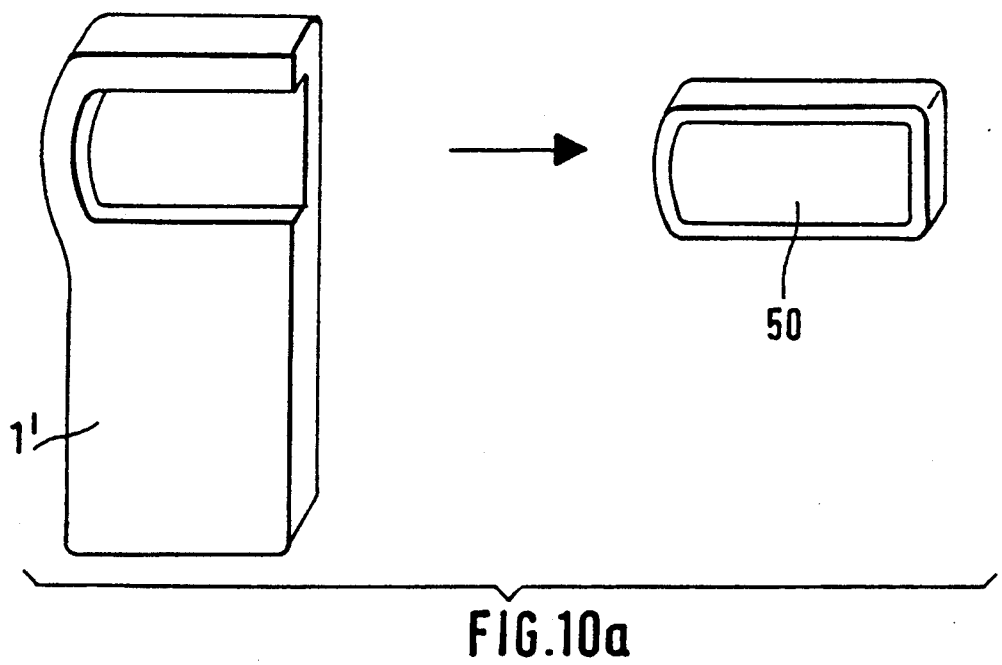
Figure 10B:
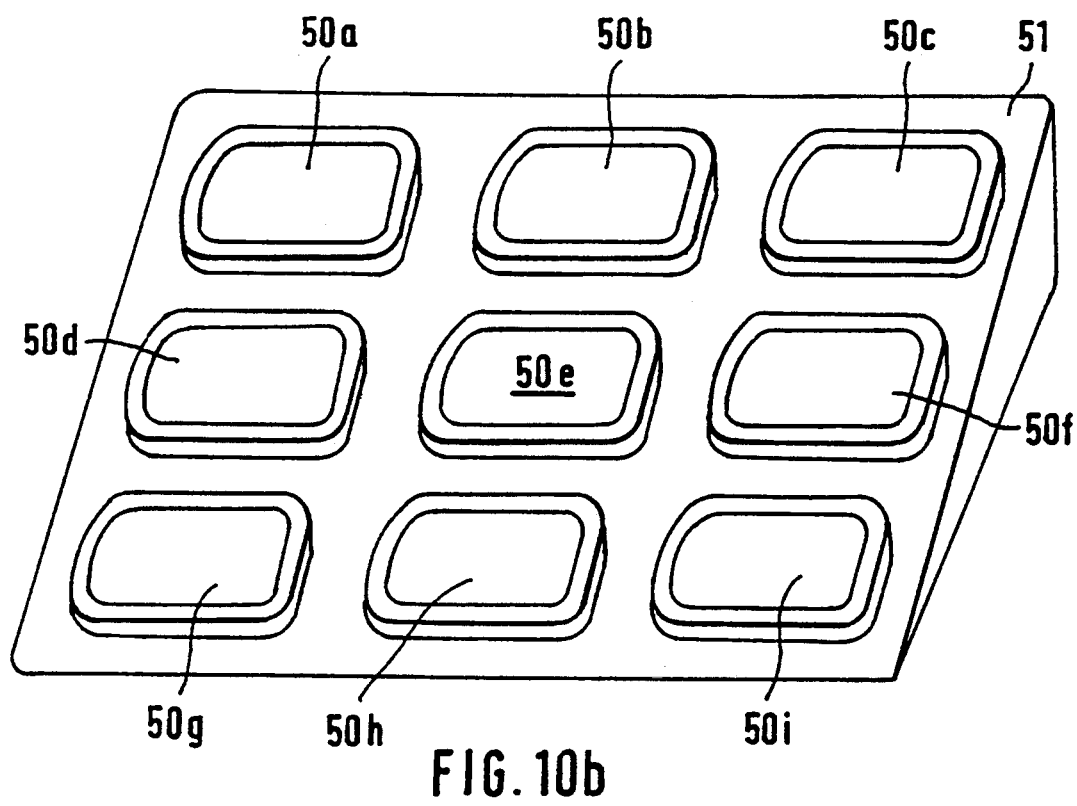
Figure 11A:
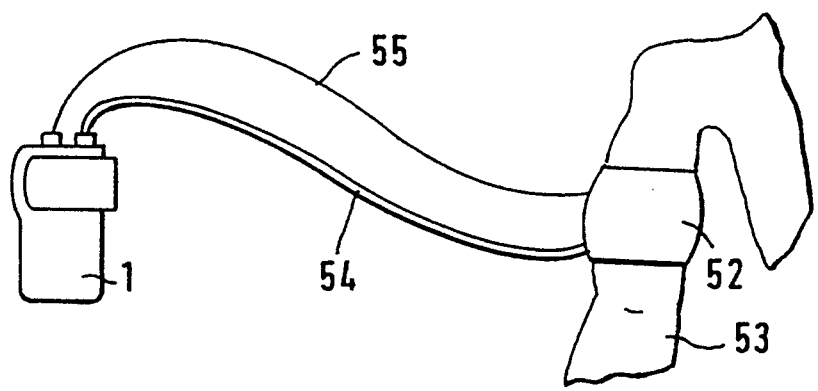
Figure 11B:
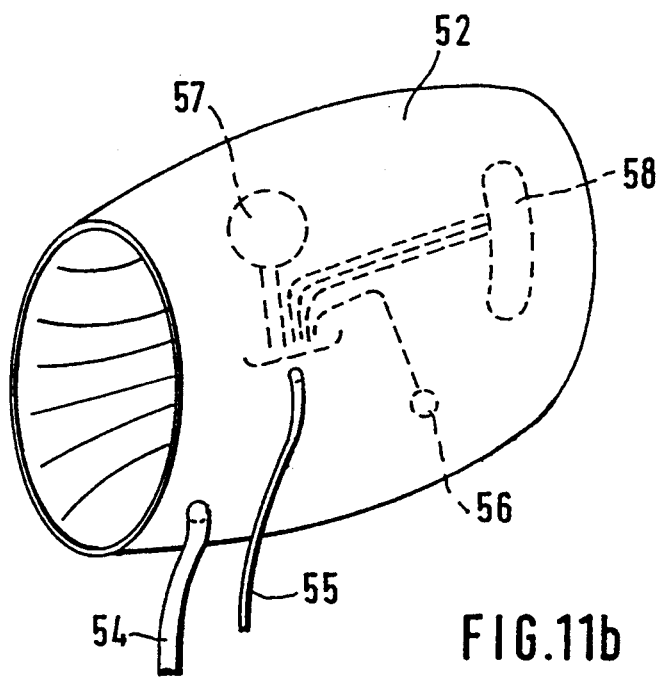
Figure 11C:
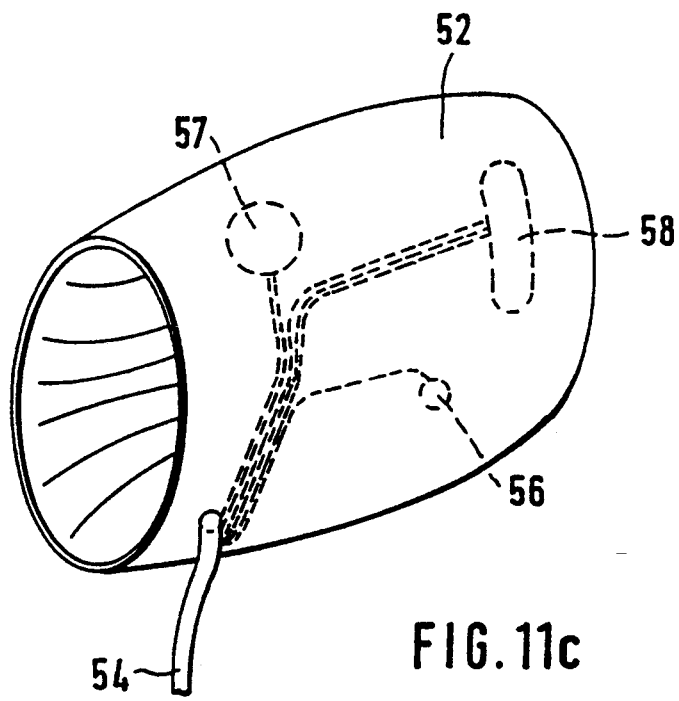
Figure 12:
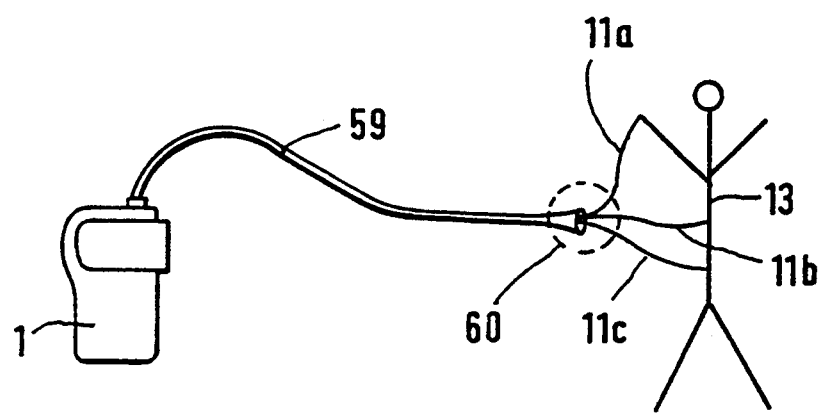

The invention will now be explained, by way of a non-limiting example, with reference to the accompanying drawings, in which:

FIG. 1 depicts a schematic diagram of a portable hand-held monitor and a combiner, FIG. 2a shows the basic interconnection scheme between the portable hand-held monitor and a patient, whereas FIG. 2b depicts the interconnection of the portable hand-held monitor with a remote computer, FIG. 3 is the top view of a portable hand-held monitor, FIG. 4 is a corresponding view from the rear, FIG. 5a depicts a combiner, FIG. 5b shows the combiner of FIG. 5a in the direction of arrow Vb, FIG. 6 is a perspective view of another combiner and its attachment to a rod, FIG. 7 depicts a base station, FIG. 8 shows the connection scheme between a portable hand-held monitor and a patient in case a wireless transmission is provided, FIG. 9 is an interconnection scheme with electrical and pneumatic cables, FIG. 10a depicts a portable hand-held monitor with removable display/memory unit, FIG. 10b illustrates a remote station with a multiplicity of slots for receiving removable display/memory units, FIG. 11a shows the interconnection scheme between a portable hand-held monitor and a cuff, FIG. 11b is a detailed perspective view of the cuff used in the embodiment of FIG. 11a, FIG. 11c depicts an alternative embodiment of a cuff, and FIG. 12 depicts an alternative interconnection scheme between a portable hand-held monitor and a patient.

In the embodiment of FIG. 1, a portable hand-held monitor for monitoring vital signs is in general designated as 1. It comprises a keyboard 2, which is only schematically indicated and may be an alphanumeric keyboard, or—preferably—a specialized keyboard which is easier to be operated by medical personnel (an example of such a keyboard will be discussed below). Portable hand-held monitor 1 further comprises a liquid crystal display 3 for displaying vital signs. In the shown example, these are the ECG (electrocardiogram) trace 4, the heart rate 5 and a temperature trace 6 (which is usually a time-compressed version called "trend", i.e., ECG trace 4, and temperature trace 6 do not have the same scaling of the time axis). It is understood that LCD display 3 may be used to display other physiological parameters and other vital signs as well.

Portable hand-held monitor 1 further comprises storage means, such as integrated circuit memories, for storing vital signs and other patient-related data. These memories are incorporated in the housing of hand-held monitor 1 and are not shown in FIG. 1.

A major feature of portable hand-held monitor 1 is the single jack 7 provided for automatic input of vital signs information. A plug 8 engages jack 7 and is in connection with a single electrical cable 9 leading to a combiner 10. A multiplicity of single cables 11a to 11d provide connection with physiological transducers (not shown in FIG. 1); for example, cables 11a and 11b could be connected with ECG electrodes, cable 11c could be connected with a temperature probe, and cable 11d could be in connection with a finger sensor for pulse oximetry. Cables 11a to 11d end up in plugs 12a to 12d which are inserted into appropriate jacks of combiner 10. The combiner combines the electrical leads so that the signals can be transmitted through a single cable 9, e.g. in parallel mode (a parallel/serial shift in combiner 10, and subsequent serial transmission via cable 9, is also possible).

It is understood that the number of plugs 12a to 12d, namely four in FIG. 1, is arbitrary. Combiner 10 could also be designed to receive three, six or any other numbers of sensor plugs. Further, the jacks of combiner 10 are not necessarily assigned to specific sensor plugs, i.e., pulse oximeter plug 12d could not only be inserted into the rightmost jack in FIG. 1; instead, the jacks or slots of combiner 10 may preferably be assignable to any possible sensor plug, such that plugs 12a to 12d could be interchanged, or that plugs of other sensors (such as respiration or blood gases) could be inserted as well.

Instead of using the single interconnection cable 9, combiner 10 could also be directly applied to jack 7. Further, combiner 10 could be connected with plug 8 via an electrical cable, as well as a pneumatic tube; such would particularly be useful in case of non-invasive blood pressure monitoring (the valves, and the pump, would be incorporated in portable hand-held monitor 1 in this case). In the latter case, the electrical cable and the pneumatic tube could be fixed to each other, and an electrical, as well as a pneumatic connector could be provided on the top of portable hand-held monitor 1. (Such an embodiment will be described below). Further, in case a pneumatic connection is required, one of the jacks or slots of combiner 10 could be a pneumatic connector specifically assigned to NIBP (non-invasive blood pressure) monitoring.

The schematical diagrams of FIGS. 2a and 2b show how portable hand-held monitor 1 may be used for patient monitoring. In the example of FIG. 2a, portable hand-held monitor 1 is connected via cable 9 with combiner 10. The combiner is placed or fixed near or at the bed of a patient 13. A multiplicity of sensor cables 11a to 11d interconnect combiner 10 with sensors or transducers applied to or attached to patient 13. In the embodiment shown in FIG. 2a, portable hand-held monitor 1 is ready for data acquisition, i.e. for acquiring vital signs information, which can be stored in the internal memory of portable hand-held monitor 1, as well as be displayed on its built-in liquid crystal display 3.

FIG. 2b illustrates the environment in the nurse's office. Portable hand-held monitor 1 is placed on an appropriate support of base unit 14. A connector at the bottom side of portable hand-held monitor 1, as well as a corresponding connector on the top of base station 14, engage when the hand-held monitor is put on the support of the base station. The connectors (not shown in FIG. 2b) serve a two-fold purpose: First, data transmission from and to the portable hand-held monitor is established and, second, a rechargeable battery pack contained in the hand-held monitor is recharged.

Base station 14 is connected (line 15) with a personal computer or terminal 16 which, in turn, may be connected with a hospital network (not shown). The data communication link is used to "download" (from the portable hand-held monitor 1 to personal computer 16) vital signs information, and to "upload" (from personal computer 16 to portable hand-held monitor 1) patient data like the patient's name, a patient identifier or details of his case history.

When the nurse starts to make her round, she will first "upload" the patient-related data of all patients she intends to visit, i.e. the patient names etc. will be transferred from personal computer 16 to portable hand-held monitor 1. Next, she will detach the hand-held monitor from base station 14 (FIG. 2b).

She will then visit the first patient. The sensors, sensor cables and the combiner remain at or near the patient's bed, as well as cable 9 (FIG. 2a). Therefore, the nurse has simply to insert the plug of cable 9 into the appropriate jack of portable hand-held monitor 1. She may then recall the name or the identifier of the patient actually connected, e.g. by pressing an appropriate button of the hand-held monitor. Vital signs of the patient are now transmitted and displayed on liquid crystal display 3. A further keystroke initiates storing of collected vital signs information, or of parameters derived therefrom. At the end of the recording sequence, the patient is disconnected by simply withdrawing the plug of cable 9. The next patient may now be monitored in the same manner, and so on.

It is understood that the portable hand-held monitor may also generate an alarm in case that one of the patient's vital signs exceeds predefined limits. Such limits may be entered via the portable hand-held monitor's keyboard, or be "uploaded" from a base or remote station.

When the nurse has finished her round, she returns to her office and puts portable hand-held monitor 1 onto the appropriate support of base station 14 (FIG. 2b). Electrical contact to base station 14 is now established in the manner described above. The collected vital signs information of various patients is transmitted, via line 15, to personal computer 16. At the same time, the internal batteries of portable hand-held monitor 1 are recharged.

It is understood that the above described method of patient monitoring is not restricted to application by a nurse. Instead, the portable hand-held monitor 1 could also be used in a doctor's practice, or the like.

It is important to note that the concept of "uploading" patient information from the remote or hospital computer to the portable hand-held monitor may also be expanded. That is, not only patient identifiers or the like could be uploaded into the portable hand-held monitor, but also other data of interest, for example the nurse's schedule. Thus, the nurse could always check her schedule, for example via the built-in display of the portable hand-held monitor. An automatic alarm (e.g., optical—via the built-in display—and/or acoustic—via a built-in piezoelectric crystal) may further remind the nurse of appointments and deadlines.

The data "uploaded" into the portable hand-held monitor could also be a patient care plan, i.e., medications and other treatments prescribed by the doctor. The portable hand-held monitor could then remind the nurse automatically of medicines etc. to be applied to the patient as soon as she calls the patient up or connects him.

This concept may even be expanded further. The portable hand-held monitor could compare the nurse's activities with the patient care plan and remind her, or cause otherwise an alarm, if she misses anything. In case the nurse is supposed to confirm or acknowledge certain activities, e.g. patient treatment, via the keyboard of the portable hand-held monitor, such acknowledgement could be stored and later be transmitted, via the base station, to a personal computer in the nurse's office, or to a hospital computer (an embodiment with removable memory modules and a remote station suited to transmit such a protocol will also be described later). The personal or hospital computer may then document the fact that the patient has appropriately been treated, e.g., generate a printout, such that a complete history of patient treatment, and control over performed measures, is available.

FIG. 3 depicts a more detailed top view of portable hand-held monitor 1. The liquid crystal display is designated as 3, as in the former figures. Five buttons 17a to 17e are used to control operation of the hand-held monitor. For example, one of these buttons or keys could be used to recall the patient names, a second one could be used to move a cursor from patient to patient, and a third one could serve to select a specific patient. Another one could be used to initiate the storing cycle, and so on.

Further provided are a power button 18 and a single connector 7. Plug 8, which fits into connector or jack 7, is a multi-pin plug, as it is known in the art. Cable 9 is only shown partially. The housing of the portable hand-held monitor is generally designated as 19.

FIG. 4 depicts the rear side of portable hand-held monitor 1, wherein the same reference numbers have been used as in the preceding drawings. It will be noted that a connector 20 is provided which, when the portable hand-held monitor is at rest on the base station, engages with a corresponding connector at the top side of the base station, in order to establish data transmission and recharging paths, as described above. A removable door 21 covers a rechargeable battery pack. Further, a suspension eye 22 may be used to hang up the portable hand-held terminal 1 if required. For this purpose, suspension eye 22 is slidably supported, as indicated by arrow 23.

One example of a combiner according to the present invention is shown in FIG. 5a. It consists of a main housing 24 provided with a single cable 25 for interconnection with the portable hand-held monitor (this cable corresponds to cable 9 in the preceding figures). Several plugs 26a to 26e are inserted into corresponding jacks of combiner 24. The plugs 26a to 26e are connected with cables 27a to 27e which, in turn, establish electrical contact to single sensors or transducers (not shown in FIGS. 5a and 5b). A tube or hose 28 connects combiner 24 with a cuff for non-invasive measurement of blood pressure; a pneumatic connector 29 is provided therefor.

FIG. 5b depicts in more detail the jacks for insertion of plugs 26a to 26e. By way of example, one of these jacks is referred to as 30a and 30b. It will be noted that the openings have been selected such (opening 30a rectangular and opening 30b circular) that the corresponding plugs can only be inserted in the correct position.

FIG. 6 depicts another example of a combiner 31 according to the present invention. In this embodiment, its housing is provided with a clamp 32 for attachment to a rod 33 which may be positioned near, or attached to, the patient's bed. Interconnection cable 34 (which leads to the portable hand-held monitor), plugs 35a to 35e and cables 36a to 36e (which lead to the single sensors or transducers) are similar to those already discussed above.

An example of a base station, generally designated as 37, is shown in FIG. 7. It consists of three detachable parts 37a, 37b and 37c. Part 37a provides a support 38 for portable hand-held monitor 1. In the shown position, electrical contact between the base station and the hand-held monitor is established.

Part 37b houses a strip chart recorder for immediate printout of vital signs information. This is particularly useful if no remote computer is connected, or if there is not sufficient time to wait for a printout of the remote computer. In the shown example, an ECG trace 39 and a temperature trace 40 are recorded on recorder paper 41. The recorder paper may e.g. be thermal paper or the like.

Part 37c is an accessories housing which houses equipment regularly used by the nurse when she is caring for patients, like a stethoscope, and so on. It may be opened by a handle 42.

In the embodiment of FIG. 8, the interconnection between portable hand-held monitor 1 and patient 13 is performed by means of wireless transmission. Again, several sensors are applied to patient 13, the sensors being connected by sensor cables 11a to 11d with a combiner 43. However, in this embodiment, the combiner 43 contains a wireless transmitter, such as a radio, ultrasound, or infrared light transmitter. Portable hand-held monitor 1 contains a corresponding receiver. It will be appreciated that the wireless link, indicated by numeral 44, also constitutes a link, or linking means, in the sense of the present invention. Such an arrangement may be particularly useful if a multiplicity of patients are subject to monitoring, as it is not necessary to establish a cable link for any of the patients.

An alternative embodiment incorporating non-invasive blood pressure sensing means is depicted in FIG. 9. A tube 45 and a cable 46 connect the combiner 10 with portable hand-held monitor 1. Tube 45 and cable 46 are held together by elastic strips 47 or the like, in order to avoid that they have to be handled separately. They end at respective connectors 48 and 49 of portable hand-held monitor 1, wherein connnector 48 is a pneumatic connector, and connector 49 is an electrical one. Although two connectors 48 and 49 are used in this embodiment, it will be appreciated that still only a single electrical connector is required. Furthermore, it is possible to have tube 45 and electrical cable 46 not as separate connections, but rather to integrate the electrical leads into the walls of the pneumatic tube. In the latter case, no strips 47 are required.

FIG. 10a depicts a portable hand-held monitor 1' with removable display/memory section 50. The memory in display/memory section 50 may e.g. contain vital signs information previously gathered from a patient.

As FIG. 10b shows, a multiplicity of display/memory sections (or modules) 50a to 50i may be inserted into a remote station 51. The remote station may for example be installed in the nurse's room and be connected with a central computer, e.g., a hospital computer. Each display/memory section 50a to 50i may be assigned to a specific patient, or to a group of patients (e.g., one display/memory section for all patients in a specific room).

The remote station 51, or the remote computer to which it may be connected, is programmed to "upload" vital signs information from all of the display/memory sections. Further, it may be programmed to "download" patient information, patient care-related information or the like into the various display/memory sections.

Before or during making her round, the nurse collects the display/memory sections of the patients she wants to visit. Patient care information, such as necessary medication, is already stored in these display/memory sections. When she has made, or prior to making, the appropriate connection with a specific patient (via a cable, or telemetric transmission, as described above), she puts this patient's display/memory module into her portable hand-held monitor. She may control now the necessary medications, apply them to the patient, and acknowledge it on her portable hand-held terminal. The confirmation that the patient has got its medicine is stored in the patient's display/memory module and later transmitted to the remote station (or a connected hospital hospital computer), when the display/memory module has been put in a slot of remote station 51 again.

Further, the patient's vital signs information is loaded into the display/memory module, and later also transmitted to the remote station/hospital computer.

The remote station 51 may not only be located in the nurse's office. She may, e.g., also carry it on a cart which she is taking with her during her round. This makes selection of patient display/memory modules easier, as less preparation has to be done in advance. In such a case, but not limited to it, nor as a necessary prerequisite thereof, it is advantageous to have the remote station 51 connected with a hospital computer via a telemetric link.

Further, it is understood that the above described concept also operates when only a memory module is made removable. The display need not necessarily be part of the removable module.

Another possibility is that the nurse enters necessary orders via the keyboard of the portable hand-held monitor. These orders are later transmitted to a personal computer or hospital computer, or some other remote system, and appropriately processed.

FIG. 11a depicts another concept of linking the portable hand-held monitor 1 with a patient. A cuff 52 is applied to the patient's arm 53. The cuff is connected with portable hand-held monitor 1 via a pneumatic tube 54 and an electrical cable 55 (which may be combined in the way FIG. 9 shows; a single pneumatic cable with the electrical leads integrated into its walls, as described above, may be used instead).

FIG. 11b depicts details of cuff 52. Pneumatic tube or hose 54 is used to inflate and deflate the cuff, as is known in the art. Various electrodes, which come into contact with the skin of the patient's arm as soon as the cuff is applied, are arranged at the inner wall of the cuff. These are, by way of example, an electrocardiogram electrode 56 and a respiration electrode 57. A reflection oximetry sensor 58 is also provided which irradiates electromagnetic readiation into the tissue (e.g. by means of a light-emitting diode) and measures the backscattered light.

The electrical leads of electrodes 56 and 57, as well as oximetry sensor 58, are laid in the inner or outer wall of cuff 52. They are all fed to electrical cable 55 which connects the cuff with the portable hand-held monitor.

The major advantage of such a cuff is that only very few sensors have to be applied to the patient—in the minimum configuration, only the cuff itself, plus an additional electrocardiogram electrode. It is understood that in this embodiment the cuff itself operates as the combining means.

A slightly different cuff configuration is depicted in FIG. 11c. In this embodiment, all of the electrical leads are fed to the pneumatic connection. The electrical leads are further fed through the walls of pneumatic tube 54, such that no additional electrical cables are required.

Yet another embodiment of the present invention is shown in FIG. 12. Again, several sensors or transducers are applied to the patient. Their respective electrical leads 11a to 11c are fed into a common cable or sheath 59. In this embodiment, the opening of cable 59 (indicated by reference number 60) acts as a combiner, i.e., is a combining means.

We claim:

1. A method for retrieving and/or monitoring vital signs of a patient, wherein $n \geq 2$ sensors comprising electrocardiogram electrodes, a temperature sensor and/or a cuff for measuring non-invasive blood pressure, are connected to connection means and are applied to a patient, comprising the steps of:

connecting at least 2 of said connection means to a combining means;

linking said combining means to a portable, hand held electronic data acquisition unit via m releaseable connector(s), $m < n$ both m and n being integers, said releasable connector(s) directly connected to said data acquisition unit by cable(s);

retrieving vital signs information from at least one of said n sensors and transmitting said vital signs information via said combining means and releasable connector(s), to said electronic data acquisition unit; and displaying said vital signs information on a display contained in said portable electronic data acquisition unit.

2. A method according to claim 1 further comprising the step of:

storing said vital signs information in said portable, hand held electronic data acquisition unit.

3. A method according to claim 2, said method comprising the further steps of connecting said portable, hand held, electronic data acquisition unit to a remote computer; and transmitting said vital signs information stored in said, hand held, portable electronic data acquisition unit at least partially to said remote computer.

4. A method according to claim 2, said method comprising the further steps of:

connecting said portable, hand held, electronic data acquisition unit to a remote computer;

transmitting data from said remote computer to said portable, hand held, electronic data acquisition unit; and storing said data in said portable hand held electronic data acquisition unit.

5. A method according to claim 4, wherein said data is patient information, patient care-related information, alarm and/or scheduling information.

6. A method according to claim 5, wherein said portable, hand held electronic data acquisition unit generates an alarm if patient care is due, and accepts and stores a confirmation on effected patient treatment.

7. A method according to claim 2, wherein a memory module includes a memory, said method comprising the further step of:

8. A system for retrieving and/or monitoring a multiplicity of vital signs of a patient, comprising:

$n \geq 2$ sensors, where n is an integer, for application to the patient;

$n \geq 2$ connection means, each of said connection means connected to one of said n sensors;

combining means for releasable connection with at least two of said connection means; and a portable, hand held electronic data acquisition unit releasably connected to said combining means via m releasable connectors, where m is an integer and $m < n$ for retrieving data from said sensing means, said data acquisition unit including a display for displaying said vital signs.

9. A system according to claim 8 wherein said combining means comprises an inflatable cuff usable for non-invasive blood pressure measurement, said cuff including at least one of an electrocardiogram electrode a respiration electrode, or an oxygen saturation sensor.

10. A system according to claim 8 wherein said electronic data acquisition unit includes memory means for storing data indicative of said vital signs.

11. A system according to claim 10, wherein said electronic data acquisition unit is a portable electronic data acquisition unit and includes a base station that is connectable with said portable electronic data acquisition unit, said base station including support means for said portable electronic data acquisition unit.

12. A system according to claim 11, wherein said support means includes automatic electrical connection means for mating with said portable electronic data acquisition unit.

13. A system according to claim 11, wherein said portable electronic data acquisition unit includes at least one rechargeable battery, and said automatic electrical connection means including automatic battery recharging connection means.

14. A system according to claim 11 wherein said base station and said portable electronic data acquisition unit enable transmission of at least part of said vital signs information from said portable electronic data acquisition unit to said base station.

15. A system according to claim 11 wherein said base station and said portable electronic data acquisition unit enable transmission of patient data, patient care-related data, alarm or scheduling information from said base station to said portable electronic data acquisition unit.

16. A system according to claim 15 wherein said electronic data acquisition unit generates an alarm signal when an alarm time occurs or has expired, or when patient care has not been acknowledged timely.

17. A system according to claim 10 wherein said memory means is removable together with said display and is insertable into a remote station containing a multiplicity of insertion slots.

* * * * *

UNITED STATES PATENT AND TRADEMARK OFFICE
CERTIFICATE OF CORRECTION

PATENT NO.  : 5,343,869
DATED       : September 6, 1994
INVENTOR(S) : Pross et al.

It is certified that error appears in the above-identified patent and that said Letters Patent is hereby corrected as shown below:

In col. 16, claim 7, line 3, after ":" (the colon) should appear --removing said memory module and inserting it into a remote station--.

Signed and Sealed this

Thirteenth Day of December, 1994

Attest:

BRUCE LEHMAN

*Attesting Officer*     *Commissioner of Patents and Trademarks*